United States Patent

Kimura

Patent Number: 5,177,264
Date of Patent: Jan. 5, 1993

[54] PROCESS FOR PREPARING AN N-SUBSTITUTED (METH)ACRYLAMIDE DERIVATIVE

[75] Inventor: Yasuhiro Kimura, Tokyo, Japan

[73] Assignee: Ajinomoto Co., Inc., Tokyo, Japan

[21] Appl. No.: 763,219

[22] Filed: Sep. 20, 1991

Related U.S. Application Data

[63] Continuation-in-part of Ser. No. 615,311, Nov. 19, 1990, abandoned.

[51] Int. Cl.$^5$ ............................................ C07C 235/00
[52] U.S. Cl. ...................................... 564/205; 564/208
[58] Field of Search ........................... 564/134, 205, 208

[56] References Cited

U.S. PATENT DOCUMENTS 3,813,438  5/1974  Oshima et al. ....................... 564/134

Primary Examiner—Alan Siegel
Attorney, Agent, or Firm—Oblon, Spivak, McClelland, Maier & Neustadt

[57] ABSTRACT

An N-substituted dialkylacetal (meth)acrylamide of formula II:

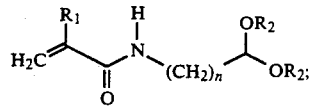

wherein n represents 3 or 4; $R_1$ represents hydrogen or methyl; and $R_2$ represents an alkyl of 1 to 3 carbon atoms is prepared by thermally decomposing an aminoacetal derivative represented by Formula I:

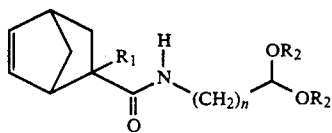

wherein n, $R_1$ and $R_2$ are as defined above, in the presence of a base.

5 Claims, No Drawings

PROCESS FOR PREPARING AN N-SUBSTITUTED (METH)ACRYLAMIDE DERIVATIVE

CROSS REFERENCE TO RELATED APPLICATIONS

The present application is a continuation-in-part of application Ser. No. 07/615,311 filed Nov. 19, 1990.

BACKGROUND OF THE INVENTION

1. Field of the Invention

The present invention relates to a process for preparing an N-substituted dialklacetal (meth)acrylamide derivative which is useful as an adhesive, a coating agent or a crosslinking agent.

2. Description of the Background

N-substituted (meth)acrylamide derivatives represented by Formula II:

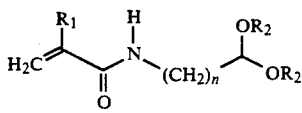

are compounds contain acrylamide and acetal groups within the molecule. Japanese Patent Application Laid-Open Nos. 61-227552, 62-36405, etc. disclose that the compounds are useful as diol-reactive crosslinking monomers. However, no useful industrial process for preparing the N-substituted (meth)acrylamide derivatives has yet been established.

In general, N-substituted (meth)acrylamides are synthesized by various processes, but the processes are automatically restricted since the compounds contain an extremely reactive acetal group within the molecule. The simplest process for synthesis comprises reacting (meth)acrylic acid chloride with an aminoacetal represented by Formula III shown below. However, this process is not suitable for industrial scale production because expensive (meth)acrylic acid chloride is used.

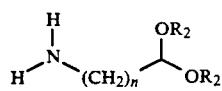

Substituent $R_2$ represents an alkyl group having 1 to 3 carbon atoms.

Direct aminolysis of less expensive (meth)acrylic acid, (meth)acrylic acid ester and (meth)acrylamide with the aminoacetal causes Michael's addition of amine to the double bond. The yield of the desired product by this technique is poor which makes the process industrially unattractive. A known modification of the reaction is to previously subject the double bond of the (meth)acrylic starting material to Michael's addition using a nucleophilic reagent such as an amine, an alcohol, or the like in order to protect the double bond. For example, methanol can be added to methyl acrylate, and then aminolysis of the resulting product with an amine is performed. The product is thermally decomposed thereby removing methanol, to give the desired N-substituted acrylamide. An attempt to synthesize the acrylamide derivatives of Formula II according to this process is shown in Japanese Patent Application Laid-Open No. 3-120244. However, the protection of the double bond by Michael's addition is not perfect. That is, upon aminolysis, substitution of the protective group for the amine of the substrate occurs and by-products, as in direct aminolysis, are eventually produced. Therefore, a problem with this process is the reduced yield of the desired N-substituted acrylamides.

Apart from this process, a process for protecting the double bond of the acryloyl group with cyclopentadiene, or the like is known. Specifically, the process comprises reacting methyl acrylate with cyclopentadiene to prepare the Diels-Alder adduct, then performing aminolysis with an amine and subjecting the product to thermal decomposition (reverse Diels-Alder reaction) to give the desired N-substituted acrylamides. According to this process, by-products are hardly produced upon aminolysis and hence, the procedure is suitable for protection of the double bond, whereby the N-substituted acrylamides can be obtained in a high yield. On the other hand, however, severe conditions for removing the protective group are required, in comparison to the aforesaid process for protecting the double bond by Michael's addition. Japanese Patent Application Laid-Open Nos. 47-34311, 49-66625 and 49-69655 disclose the synthesis of N-substituted acrylamides of simple chain amines and cyclic amines having a relatively low molecular weight, but are completely silent on compounds shown by Formula II which contain a reactive group therein.

The aminoacetal derivative can be synthesized according to the process disclosed in Japanese Patent Application Laid-Open No.2-306950. The problem with this approach is the production of by-products resulting from the intermolecular or intramolecular condensation of the acetal group. A need therefore continues to exist for an improved method of producing N-substituted dialkylacetal (meth)acrylamide derivatives.

SUMMARY OF THE INVENTION

Accordingly, one object of the present invention is to provide a method of producing N-substituted dialkylacetal (meth)acrylamide in improved yields.

Briefly, this object and other objects of the present invention, as hereinafter will become more readily apparent, can be attained in a process for preparing an N-substituted dialkylacetal (meth)acrylamide of Formula II;

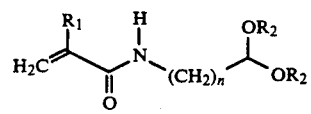

by thermally decomposing an aminoacetal derivative of Formula I:

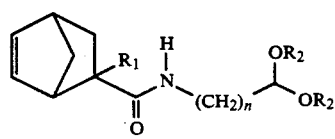

wherein n represents 3 or 4; $R_1$ represents hydrogen or methyl; and $R_2$ represents an alkyl having 1 to 3 carbon atoms, in the presence of a base.

DESCRIPTION OF THE PREFERRED EMBODIMENTS

As a result of extensive investigations on the process for preparing an N-substituted dialkylacetal (meth)acrylamide via the Diels-Alder reaction, the conditions have now been found under which the product can be obtained in high yield. The key aspect of the present invention is that the N-substituted dialkylacetal (meth)acrylamide of Formula II is effectively prepared by thermally decomposing the aminoacetal derivative of Formula I, during the course of preparing the N-substituted dialkylacetal (meth)acrylamide from the aminoacetal derivative, in the presence of a base.

It has been found that side reactions involving intramolecular and intermolecular condensation reactions of the acetal group, which tend to readily occur, depending upon reaction conditions, can easily be prevented with certainty by conducting the thermal decomposition reaction in the presence of base. Suitable bases which can be used in the present invention include inorganic bases such as sodium carbonate, sodium hydrogencarbonate, sodium hydroxide, potassium hydroxide, calcium hydroxide, and the like; and organic bases such as a tertiary amines, pyridine, and the like. In addition, alcoholates of alkali metals or hydrides of alkali metals used as the catalyst for aminolysis may also be used as the base. In order to prevent polymerization of the product, polymerization inhibitors such as hydroquinone, p-methoxyphenol, benzoquinone, 2,6-t-butyl-p-cresol, 2,3-dimethyl-6-t-butylphenol, anthraquinone, phenothiazine, tocopherol, and the like should preferably be present during the decomposition reaction.

The thermal decomposition reaction should preferably be conducted in the gaseous phase. For this reaction, an ordinary device for flash vacuum pyrolytic decomposition may be used. That is, a stream of the aminoacetal derivative is passed under reduced pressure through a reaction tower packed with a filler such as Raschig rings or the like and is heated at 200° to 800° C. to decompose the aminoacetal derivative. Among the decomposition products, the desired N-substituted (meth)acrylamide derivative is chilled with water to selectively condense and collect the desired product. Cyclopentadiene, which is another decomposition product of low melting point, is recovered by a trap cooled with liquid nitrogen, or the like.

The yield of the desired product N-substituted dialkylacetal (meth)acrylamide, depends on several factors which are the temperature of decomposition, the surface of the packing material and the vapor velocity of the desired products passing through the reaction tower.

A rich harvest of a desired product is obtained by conducting the decomposition reaction at high temperature of
about 500°-700° C., thermally decomposing the Diels Alder product on the surface of the packing material having a large surface area and packed in a reaction tower or by thermally decomposing the Diels Alder product under the condition of low line-velocity of the vapor of the aminoacetal derivative passing through the reaction tower. Of course, combinations of these decomposition conditions are effective measures in obtain the desired product. The reverse Diels-Alder reaction does not occur under these conditions.

Having generally described this invention, a further understanding can be obtained by reference to certain specific examples which are provided herein for purposes of illustration only and are not intended to be limiting unless otherwise specified.

REFERENCE EXAMPLE 1

While stirring, 175 g of cyclopentadiene was gradually added dropwise to 207 g of methyl acrylate, and the temperature of the reaction mixture was kept at 25° to 30° C. After completion of the dropwise addition, the reaction mixture was stirred below 30° C. overnight. Distillation under reduced pressure gave 356 g of methyl norbornenecarboxylate. To 304 g of this compound were added 266 g of 4,4-dimethoxybutylamine and 19 g (5 mol % based on substrate) of sodium methoxide in 28% methanol solution. The mixture was heated with stirring for 6 hours in an oil bath at 120° C. After allowing the reaction mixture to cool, 200 ml of water and 1 liter of dichloromethane were added to the reaction mixture. After hydrochloric acid was added in an amount necessary to neutralize the aqueous phase, the organic layer was separated from the aqueous phase. Dichloromethane was removed by distillation from the organic phase to give 440 g of 5-N-(4,4-dimethoxybutyl)carboxamido-2-norbornene (99% pure by gas chromatography).

EXAMPLE 1

After 1.2 g (corresponding to 5 mol % based on substrate) of sodium carbonate was added to 60 g of 5-N-(4,4-dimethoxybutyl)-carboxamido-2-norbornene obtained in Reference Example 1, the mixture was heated under reduced pressure of 1.1 torr to vaporize the compound. The vapor stream was passed into a reaction tower (diameter of 2 cm and length of 25 cm) packed with Raschig rings and kept at 300° C. to cause thermal decomposition of the compound. Next, the decomposition products were passed through a cooler chilled with water to collect the product of high boiling point and then cyclopentadiene, as the decomposition product of a low boiling point, respectively, in traps in a liquid nitrogen bath. The high boiling decomposition product was analyzed by gas chromatography. The results are shown in Table 1.

EXAMPLE 2

After 1.2 g (corresponding to 5 mol % based on substrate) of sodium carbonate was added to 60 g of 5-N-(4,4-dimethoxybutyl)-carboxamido-2-norbornene prepared as described in Reference Example 1, the mixture was thermally decomposed at 300° C. under reduced pressure of 1.2 torr in the gaseous phase, as described in Example 1. The high boiling decomposition product was analyzed by gas chromatography. The results are shown in Table 1.

EXAMPLE 3

After 1.2 g (corresponding to 5 mol % based on substrate) of sodium carbonate was added to 60 g of 5-N-(4,4-dimethoxybutyl)carboxamido-2-norbornene prepared as described in Reference Example 1, the mixture was thermally decomposed at 400° C. under reduced pressure of 1.4 torr in the gaseous phase, as described in Example 1. The high boiling decomposition product was analyzed by gas chromatography. The results are shown in Table 1.

EXAMPLE 4

After 1.2 g (corresponding to 5 mol % based on substrate) of sodium carbonate was added to 60 g of 5-N-(4,4-dimethoxybutyl)carboxamido-2-norbornene prepared as described in Reference Example 1, the mixture was thermally decomposed at 400° C. under reduced pressure of 1.2 torr in the gaseous phase, as described in Example 1. The high boiling decomposition product was analyzed by gas chromatography. The results are shown in Table 1.

EXAMPLE 5

After 1.2 g (corresponding to 5 mol % based on substrate) of sodium carbonate was added to 60 g of 5-N-(4,4-dimethoxybutyl)carboxamido-2-norbornene prepared as described in Reference Example 1, the mixture was thermally decomposed at 500° C. under reduced pressure of 1.2 torr in the gaseous phase, as described in Example 1. The high boiling decomposition product was analyzed by gas chromatography. The results are shown in Table 1.

EXAMPLE 6

After 1.2 g (corresponding to 5 mol % based on substrate) of sodium carbonate was added to 60 g of 5-N-(4,4-dimethoxybutyl)-carboxamido-2-norbornene prepared as described in Reference Example 1, the mixture was thermally decomposed at 600° C. under reduced pressure of 1.2 torr in the gaseous phase, as described in Example 1. The high boiling decomposition product was analyzed by gas chromatography. The results are shown in Table 1.

COMPARATIVE EXAMPLE 1

Using the same reaction apparatus as described in Example 1, 60 g of 5-N-(4,4-dimethoxybutyl)carboxamido-2-norbornene obtained in Reference Example 1 was thermally decomposed at a decomposition temperature of 300° C. under reduced pressure of 1.8 torr without adding any base. The high boiling decomposition product was analyzed by gas chromatography. The results are shown in Table 1.

of Formula II can be prepared in high yield without significant by-product formation.

Having now fully described the invention, it will be apparent to one of ordinary skill in the art that many changes and modifications can be made thereto without departing from the spirit or scope of the invention as set forth herein.

WHAT IS CLAIMED AS NEW AND DESIRED TO BE SECURED BY LETTERS PATENT OF THE UNITED STATES IS:

1. A process for preparing an N-substituted dialkylacetal (meth)acrylamide of Formula II:

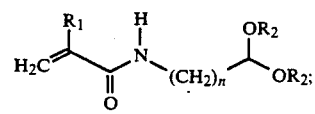

wherein n represents 3 or 4; $R_1$ represents hydrogen or methyl; and $R_2$ represents an alkyl of 1 to 3 carbon atoms which comprises:

thermally decomposing an aminoacetal derivative represented by Formula I:

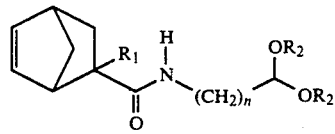

wherein n, $R_1$ and $R_2$ are as defined above, in the presence of a base selected from the group consisting of sodium carbonate, sodium hydrogen carbonate, sodium hydroxide, potassium hydroxide, calcium hydroxide, a tertiary amine, pyridine and an alcoholate or a hydride of an alkali metal.

2. The process of claim 1, wherein said alkali metal is sodium, potassium or lithium.

3. A process of claim 1, wherein said N-substituted dialkylacetal (meth)acrylamide is acrylamide butylaldehyde dimethylacetal.

4. The process of claim 1, which is conducted in the presence of a polymerization inhibitor.

5. The process of claim 1, wherein the thermal decomposition reaction is conducted in the vapor phase at a temperature of 200° to 800° C.

TABLE 1

Synthesis of acrylamidobutylaldehyde dimethylacetal by thermal decomposition of 5-N-(4,4-dimethoxybutyl)carboxamido-2-norbornene

| | Reaction Tower | Decomposition Temperature (°C.) | Sodium Carbonate mol % | Degree of Reduced Pressure torr | Components of High Boiling Decomposition Products | | | Yield of A % |
|---|---|---|---|---|---|---|---|---|
| | | | | | A % | B % | C % | |
| Comp. Ex. 1 | X | 300 | 0 | 1.8 | 1 | 2 | 91 | 1 |
| Ex. 1 | X | 300 | 5 | 1.1 | 60 | 40 | 0 | 46 |
| Ex. 2 | Y | 300 | 5 | 1.2 | 96 | 4 | 0 | 80 |
| Ex. 3 | X | 400 | 5 | 1.4 | 73 | 27 | 0 | 63 |
| Ex. 4 | Y | 400 | 5 | 1.2 | 98 | 2 | 0 | 83 |
| Ex. 5 | X | 500 | 5 | 1.2 | 86 | 12 | 0 | 80 |
| Ex. 6 | X | 600 | 5 | 1.2 | 97 | 0 | 0 | 84 |

A: acrylamidobutylaldehyde dimethylacetal
B: 5-N-(4,4-dimethoxybutyl)carboxamido-2-norbornene
C: N-5-norbornen-2-oyl-2-pyroline
X: 2cmφ × 25cm L
Y: 4cmφ × 25cm L

EFFECT OF THE INVENTION

By conducting the thermal decomposition of the aminoacetal Diels-Alder compound in the presence of base, the N-substituted dialkylacetal (meth)acrylamide